United States Patent [19]
Caspar et al.

[11] Patent Number: 5,618,260
[45] Date of Patent: Apr. 8, 1997

[54] SURGICAL INSTRUMENT

[75] Inventors: Wolfhard Caspar, Contwig; Gebhard Herrmann, Irndorf; Theodor Lutze, Balgheim; Dieter Weisshaupt, Immendingen, all of Germany

[73] Assignee: Aesculap AG, Tuttlingen, Germany

[21] Appl. No.: 430,720

[22] Filed: Apr. 28, 1995

[30] Foreign Application Priority Data

Apr. 29, 1994 [DE] Germany .......................... 44 15 074.1

[51] Int. Cl.⁶ .................................................. A61B 17/02
[52] U.S. Cl. ........................................... 600/210; 600/201
[58] Field of Search ........................... 600/201, 207–220, 600/227–244; D24/135

[56] References Cited

U.S. PATENT DOCUMENTS

| | | | |
|---|---|---|---|
| D. 343,235 | 1/1994 | Levahn | D24/135 |
| 569,839 | 10/1896 | Roeloffs | 128/20 |
| 1,252,177 | 1/1918 | Redfield | 600/239 |
| 1,550,403 | 8/1925 | Turkus | 600/210 |
| 3,565,061 | 2/1971 | Reynolds | 600/210 |
| 3,729,006 | 4/1973 | Wilder et al. | 600/210 |
| 3,731,673 | 5/1973 | Halloran | 600/210 |
| 5,167,222 | 12/1992 | Schinkel et al. | 600/210 |

FOREIGN PATENT DOCUMENTS

| | | |
|---|---|---|
| 1784820 | 3/1959 | Germany . |
| 6808528 | 8/1969 | Germany . |
| 2009064 | 9/1970 | Germany . |

Primary Examiner—Richard J. Apley
Assistant Examiner—Beverly M. Flanagan
Attorney, Agent, or Firm—Barry R. Lipsitz; Ralph F. Hoppin

[57] ABSTRACT

In order to make the covered tissue areas visible in an X-ray picture when using a surgical instrument for the retention of tissue which has at least one valve held on one side, also when using a material impermeable to X-rays, it is suggested that the contact surface of the valves have openings in a distribution which leaves an increasing, non-perforated cross-sectional area from the free end of the contact surface up to its holder.

20 Claims, 1 Drawing Sheet

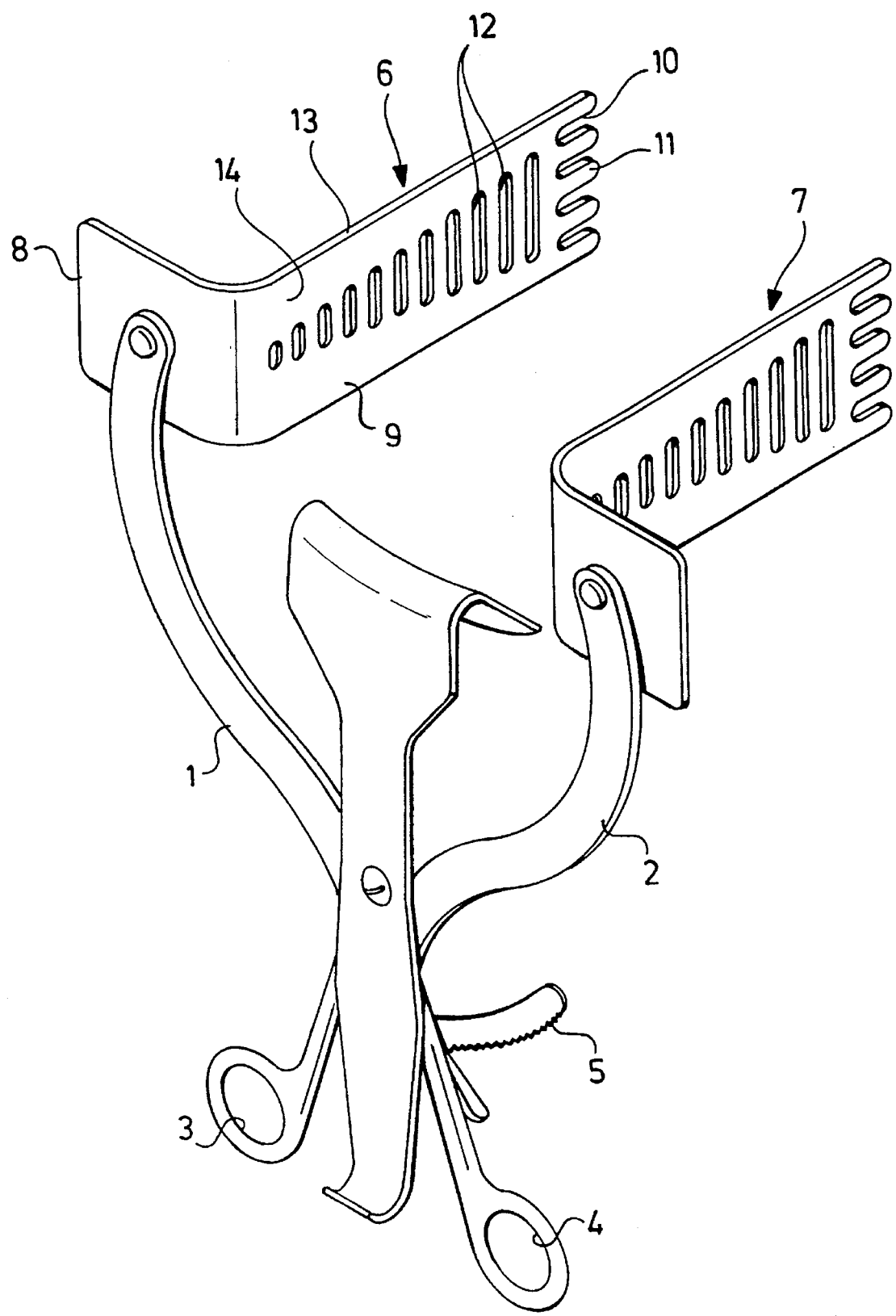

SURGICAL INSTRUMENT

BACKGROUND OF THE INVENTION

The invention relates to a surgical instrument for the retention of tissue, having at least one valve held on one side.

Instruments of this type are used, for example, in operations to open wounds and hold back organs so that operation routes can be opened up. Valves of this type normally consist of metal, and they are thus impermeable to X-rays. When an area of operation is X-rayed, the regions covered by the valves of such retaining instruments are a considerable interference since in these regions there is no visibility for X-rays at all.

Attempts have been made to overcome this disadvantage by producing the valves from a material which is transparent to X-rays or to design them to be very thin. In both cases, better possibilities do result for recognizing structures on the X-ray picture despite the valves but, on the other hand, the mechanical stability of these valves is so slight that they can no longer reliably fulfill their function.

SUMMARY OF THE INVENTION

The object of the invention is to design a surgical instrument of the generic type such that, on the one hand, the disadvantage of the complete X-ray impermeability is eliminated as far as possible while, on the other hand, the strength values necessary for the retention function are maintained.

This object is accomplished in accordance with the invention, in a surgical instrument of the type described at the outset, in that the contact surface of the valve has openings in a distribution which leaves an increasing, non-perforated cross-sectional area from the free end of the contact surface up to its holder.

The arrangement of the openings in the contact surface of the valve results in a complete transparency for X-rays at least in these regions. On the other hand, the strength of the valve is, of course, diminished by the provision of openings in the contact surface, and in this case the present invention offers a possibility of combining the advantages of the better transparency with the advantage of maintaining stability. Care is namely taken that despite the openings in the valve an unperforated area remains available which is sufficient for the retention function and in such a manner that this unperforated cross-sectional area increases from the free end of the contact surface towards the side which is held. It has surprisingly been found that due to such a distribution, in which a greater perforated cross-sectional area is possible in the vicinity of the free end than in the held part, the X-ray transparency is impaired only to a slight extent and, nevertheless, the strength can be maintained to its full extent. This is, in particular, the result of the fact that the visibility is normally required, in particular, in the region of the free end of the valve whereas, on the other hand, the strength requirements in the area close to the holder are greater, due to the one-sided holding of the valves, than in the area removed from the holder. It is, therefore, possible to provide a considerable portion of the cross-sectional area with openings and nevertheless achieve the necessary strengths.

It is favorable for the non-perforated cross-sectional area to increase essentially linearly with the distance from the free end of the contact surface.

In a preferred embodiment, it is possible for the openings to be located in a central region of the contact surface and for lateral edge regions to be provided which are arranged at the edge of the contact surface and are free of openings and have a width which increases from the free end towards the held end of the contact surface. This is particularly favorable since a transparency for X-rays is created in this way in the central region of the contact surface while a nontransparency remains only in the edge region, and in this edge region the surgeon can mentally follow the contours substantially more easily when he receives X-ray information from outside the contact surface and in the central part of the contact surface. The width of the area without X-ray information is reduced in this way to a very considerable extent in comparison with valves having a non-perforated surface.

While it is possible to design the valves to broaden from the free end towards the held end and then provide an essentially constant area of openings over the entire length, a preferred embodiment provides for the openings to be located in a triangular area which widens towards the free end of the contact surface. It is then possible to use conventional valves with a constant width, in which the openings become smaller towards the mounted end; in particular, all the openings are located in a triangular area. This can preferably have an opening angle of between 5° and 25°, in particular between 10° and 18°.

It is favorable for the openings to be slits arranged transversely to the longitudinal direction of the valves. These can have a width of between 2 and 8 mm; it is advantageous for the distance between adjacent slits to be between 1.5 and 5 mm and the length of the slits is advantageously between 30 and 90% of the valve width.

There are quite considerable advantages in performing an operation, in which it is necessary to look at the area of operation with X-rays, with an instrument of the type described in the above. Despite the use of a material for the valves which is impermeable to X-rays, it is possible to recognize the covered areas at least partially on the X-ray picture through the openings and, therefore, the necessary information for performing the operation is also given in the covered regions.

The following description of a preferred embodiment of the invention serves to explain the invention in greater detail in conjunction with the drawing. The drawing shows a retractor which is known per se and has two valves which, according to the invention, have openings within a triangular area.

BRIEF DESCRIPTION OF THE DRAWING

The FIGURE shows a perspective view of the surgical instrument in accordance with the present invention.

DETAILED DESCRIPTION OF THE INVENTION

The instrument illustrated in the drawing comprises two branches 1, 2 which are pivotally connected with one another and each have a grip opening 3, 4 and which can be pivoted against one another and fixed in position by means of a locking pawl 5. This locking pawl 5 can be released again in a manner known per se so that the branches 1 and 2 can again be moved away from one another.

Each of the two branches 1, 2 bears at its free end a valve 6, 7 L-shaped in cross section. These valves are constructed in mirror image but otherwise completely identical so that, in the following, only one of the two valves will be explained in greater detail.

This valve consists of metal, for example of titanium or a titanium alloy; it comprises a rectangular strip with an unperforated arm 8, on which the branch 1 or 2 engages, and an elongated arm 9 which is arranged at right angles thereto and extends parallel to the pivot axis of the two branches. This arm 9 has a plurality of longitudinal slits 10 at its free end such that prong-like projections 11 are formed between the longitudinal slits 10.

Slit-shaped openings 12 extending transversely to the longitudinal direction of the arm 9 are provided in the region between the unperforated arm 8 and the prongs 11 and these openings are located within a triangular area, the vertex of which is arranged at the rearward end of the arm 9, proximal to the unperforated arm 8. The opening angle of this triangular area is, in the illustrated embodiment, in the order of 15°; this triangular area widens in the direction towards the free end of the arm 9.

This means that unperforated edge strips 14 remain between the triangular area in which the openings 12 are located and the edge 13 of the arm 9 and these edge strips 14 widen accordingly from the free end of the arm 9 towards the rear end.

This distribution of the openings 12 means that the unperforated cross-sectional area increases continuously towards the fixed end so that the strength of the arm 9 in relation to bending remains constant over the entire length. At the free end, the lever arm which acts on the arm during bending stress is correspondingly shorter so that the same bending strength can be achieved even with larger openings.

The width of the longitudinal slits 10 is between 3 and 10 mm, preferably approximately 6 to 8 mm; the distance between adjacent slits is between 1 and 5 mm, preferably 1.5 to 2.5 mm.

In the illustrated embodiment, an arm is used with an arm length in the order of approximately 70 mm, a width of approximately 20 to 30 mm and a thickness in the order of 1 to 2.5 mm; the length of the foremost slit can, for example, be 17 mm, that of the rearmost slit 7 mm.

We claim:

1. Surgical instrument for the retention of tissue, having at least one valve held on one side, characterized in that the contact surface of the valve has openings in a distribution leaving a non-perforated, cross-sectional area which increases in a substantially continuous manner from the free end of the contact surface up to its holder.

2. Instrument as defined in claim 1, characterized in that the non-perforated cross-sectional area increases essentially linearly with the distance from the free end of the contact surface.

3. Instrument as defined in claim 1, characterized in that the openings are located in a central region of the contact surface and that lateral edge regions arranged at the edge of the contact surface and being free of openings are provided, the width of said edge regions increasing from the free end towards the held end of the contact surface.

4. Instrument as defined in claim 3, characterized in that the openings are located in a triangular area widening towards the free end of the contact surface.

5. Instrument as defined in claim 4, characterized in that the opening angle of the triangular area is between 5° and 25°.

6. Instrument as defined in claim 5, characterized in that the opening angle of the triangular area is between 10° and 18°.

7. Instrument as defined in claim 1, characterized in that the openings are slits arranged transversely to the longitudinal direction of the valves.

8. An instrument as defined in claim 7, wherein said slits have a substantially uniform width.

9. An instrument as defined in claim 7, wherein said slits are substantially equi-spaced along said contact surface.

10. An instrument as defined in claim 7, wherein a length of said slits varies between approximately 30% of a width of said valve near said holder to approximately 90% of a width of said valve near said free end.

11. Instrument as defined in claim 3, characterized in that the openings are slits arranged transversely to the longitudinal direction of the valves.

12. Instrument as defined in claim 7, characterized in that the slits have a width of between 2 and 8 mm.

13. Instrument as defined in claim 7, characterized in that the distance between adjacent slits is between 1.5 and 5 mm.

14. A surgical instrument for the retention of tissue comprising at least one valve held on one side;

said valve comprising a contact surface with a plurality of openings extending along a length of said contact surface from a first region proximate to a free end of said contact surface to a second region proximate to a holder of said contact surface;

said openings having respective cross-sectional areas decreasing in size substantially continuously from said first region to said second region.

15. An instrument as defined in claim 14, wherein said decrease in size of said cross-sectional areas of said openings is approximately linear with a distance from said openings to said first region.

16. An instrument as defined in claim 14, wherein:

said openings are located in a central region of said contact surface;

lateral edge regions are arranged at respective edges of said contact surface, said edge regions being free of said openings; and a width of said edge regions increases from said first region toward said second region.

17. An instrument as defined in claim 16, wherein said openings are located in a triangular area widening at an opening angle from said second region toward said first region.

18. An instrument as defined in claim 17, wherein said openings are slits arranged transversely to said length of said contact surface.

19. An instrument as defined in claim 18, wherein said slits have a substantially uniform width.

20. An instrument as defined in claim 18, wherein said openings are approximately equi-spaced along said length of said contact surface.

* * * * *